(12) United States Patent
Auchinleck

(10) Patent No.: US 8,775,209 B2
(45) Date of Patent: Jul. 8, 2014

(54) APPARATUS AND METHOD FOR ADMINISTRATION OF MOTHER'S MILK

(75) Inventor: Geof Auchinleck, Vancouver (CA)

(73) Assignee: Haemonetics Corporation, Braintree, MA (US)

( * ) Notice: Subject to any disclaimer, the term of this patent is extended or adjusted under 35 U.S.C. 154(b) by 372 days.

(21) Appl. No.: 12/083,391

(22) PCT Filed: Oct. 12, 2006

(86) PCT No.: PCT/CA2006/001675
§ 371 (c)(1),
(2), (4) Date: Apr. 9, 2008

(87) PCT Pub. No.: WO2007/045078
PCT Pub. Date: Apr. 26, 2007

(65) Prior Publication Data
US 2009/0157428 A1    Jun. 18, 2009

Related U.S. Application Data

(60) Provisional application No. 60/728,392, filed on Oct. 18, 2005.

(51) Int. Cl.
*G06F 19/00* (2011.01)
(52) U.S. Cl.
USPC ............................................................ 705/3
(58) Field of Classification Search
USPC ............ 705/2–4, 26; 600/300–301; 340/540; 235/385
See application file for complete search history.

(56) References Cited

U.S. PATENT DOCUMENTS

| | | | |
|---|---|---|---|
| 4,164,320 A | | 8/1979 | Irazoqui et al. |
| 4,953,745 A | | 9/1990 | Rowlett, Jr. |
| 5,493,107 A | * | 2/1996 | Gupta et al. .................. 235/383 |
| 5,790,409 A | | 8/1998 | Fedor et al. |
| 5,824,216 A | | 10/1998 | Joie et al. |
| 5,912,818 A | | 6/1999 | McGrady et al. |
| 5,969,606 A | * | 10/1999 | Reber et al. .................. 340/540 |
| 6,058,876 A | * | 5/2000 | Keene ........................... 116/200 |

(Continued)

FOREIGN PATENT DOCUMENTS

| CA | 2430181 | | 11/2004 |
|---|---|---|---|
| JP | 06-343679 | A2 | 12/1994 |

(Continued)

OTHER PUBLICATIONS

"Applying airline safety practices to medication administration" by Theresa M. Pape, published in MedSurg Nursing, Apr. 2003. From Dialog File 149 (TGG Health & Wellness Database).*

(Continued)

*Primary Examiner* — John Pauls

(57) ABSTRACT

Apparatus and methods are described for matching of mothers' milk to the correct baby in hospitals or other institutions where mothers' milk is expressed in advance and stored for feeding to the baby at a later time. Electronically readable indicia are used to confirm the identity of the baby, the milk units, and caregivers when the mother's milk is fed to a baby. Apparatus and methods for the collection, storage, and communication of information relevant to handling of the mother's milk are detailed such that complete audit trails are recorded and guidance to the caregiver is provided in order to ensure that all required procedures are executed properly.

14 Claims, 10 Drawing Sheets

(56) References Cited

U.S. PATENT DOCUMENTS

| | | |
|---|---|---|
| 6,346,886 B1 | 2/2002 | De La Huega |
| 6,397,190 B1 | 5/2002 | Goetz |
| 6,421,650 B1 | 7/2002 | Goetz et al. |
| 6,604,019 B2 | 8/2003 | Ahlin et al. |
| 6,618,602 B2* | 9/2003 | Levin .................. 600/323 |
| 6,983,884 B2* | 1/2006 | Auchinleck ............ 235/385 |
| 6,994,781 B2 | 2/2006 | Cork et al. |
| 7,349,858 B1 | 3/2008 | McGrady et al. |
| 7,490,767 B2* | 2/2009 | Auchinleck ............ 235/385 |
| 2002/0013523 A1* | 1/2002 | Csore et al. ............ 600/368 |
| 2002/0023441 A1 | 2/2002 | Bara |
| 2002/0095238 A1 | 7/2002 | Ahlin et al. |
| 2002/0128585 A1 | 9/2002 | Cork et al. |
| 2002/0132343 A1 | 9/2002 | Lum |
| 2002/0143320 A1 | 10/2002 | Levin |
| 2003/0009244 A1 | 1/2003 | Engleson et al. |
| 2003/0052787 A1 | 3/2003 | Zerhusen et al. |
| 2003/0055685 A1* | 3/2003 | Cobb et al. ............... 705/3 |
| 2003/0072676 A1 | 4/2003 | Fletcher-Haynes et al. |
| 2004/0039607 A1 | 2/2004 | Savitz et al. |
| 2004/0044326 A1 | 3/2004 | Kranz et al. |
| 2004/0046020 A1* | 3/2004 | Andreasson et al. ........ 235/385 |
| 2004/0108795 A1 | 6/2004 | Meek et al. |
| 2004/0113421 A1 | 6/2004 | Penuela et al. |
| 2004/0121767 A1 | 6/2004 | Simpson et al. |
| 2004/0122356 A1 | 6/2004 | Burke |
| 2004/0128162 A1 | 7/2004 | Schlotterbeck et al. |
| 2004/0143459 A1 | 7/2004 | Engleson et al. |
| 2004/0172283 A1 | 9/2004 | Vanderveen et al. |
| 2004/0176984 A1 | 9/2004 | White et al. |
| 2004/0205989 A1 | 10/2004 | Michaels |
| 2004/0230337 A1 | 11/2004 | De Gaulle et al. |
| 2004/0257231 A1 | 12/2004 | Grunes et al. |
| 2005/0019943 A1 | 1/2005 | Chaoui et al. |
| 2005/0086071 A1 | 4/2005 | Fox, Jr. et al. |
| 2005/0171815 A1 | 8/2005 | Vanderveen |
| 2005/0184153 A1* | 8/2005 | Auchinleck ............ 235/385 |
| 2006/0187003 A1* | 8/2006 | Terenna ................ 340/309.16 |
| 2007/0203802 A1* | 8/2007 | Medo et al. ............. 705/26 |

FOREIGN PATENT DOCUMENTS

| | | |
|---|---|---|
| WO | WO 00/03344 A1 | 1/2000 |
| WO | WO 0235432 A1 | 5/2002 |
| WO | WO 02/45029 A2 | 6/2002 |
| WO | WO 02/069099 A2 | 9/2002 |
| WO | WO 03/025827 A1 | 3/2003 |
| WO | WO 03/033052 A2 | 4/2003 |
| WO | WO 2004/072828 A2 | 8/2004 |
| WO | WO 2005/066872 A2 | 7/2005 |
| WO | WO 2005/067385 A2 | 7/2005 |

OTHER PUBLICATIONS

U.S. Appl. No. 12/083,392, filed Apr. 9, 2008, Auchinleck.

Precision Dynamics Corporation, PDC Europe, Patient ID Wristbands & Heathcare Products 2006 Catalog (Nov. 2004) www.pdc-media.com/downloads/2006healthcarecatalog-en.pdf.

Zebra TLP 2824 Desktop Printer User Guide (2004) www.zebra.com.

Zebra QL and QL Plus Series Mobile Printer User Guide (Mar. 2005) www.zebra.com.

R402 Smart Label Printer and Encoder User Guide (2002) www.zebra.com.

Supplies Selector Guide (Feb. 2003) www.zebra.com.

MC 50 Licensing, Patent & Regulatory Information, (Sep. 2004) ftp://symstore.longisland.com/symstore/techpubs/manuals/mobile/pdf/6786301b.pdf; www.symbol.com.

SPT 1700 Series Product Reference Guid (Dec. 2000) ftp://symstore.longisland.com/symstore/techpubs/manuals/mobile/pdf/3754403a.pdf; www.symbol.com.

Welch Allyn Imageteam 4400/4700 2D Series Hand-Held Imager User's Guide (1998) www.handheld.com/download.aspx?download-/data/032b6159-f045-4190-a52a-2e5efa74547.pdf&filename=44-4700+UG+.

P. Ashford et al., "Guidelines for Blood Bank Computing" Transfusion Medicine, 20, pp. 307-314 (2000).

R. Haggas, "Are We Transfusing the Right Patient?" The Institute of Biomedical Science, Transfusion Science, IBMS Congress (2001).

J.C.W. Chan, et al., "Use of an Electronic Barcode System for Patient Identification During Blood Transfusion: 3-Year Experience in a Regional Hospital" Hong Kong Medical Journal, vol. 10, No. 3, pp. 166-171 (Jun. 2004).

J. B. Grotting, et al., "The Effect of Barcode-Enabled Point-of-Care Technology on Patient Safety" Bridge Medical, Inc. (Oct. 2002).

* cited by examiner

APPARATUS AND METHOD FOR ADMINISTRATION OF MOTHER'S MILK

FIELD OF THE INVENTION

The present invention relates generally to apparatus and method for matching of mother's milk to the correct baby in hospitals or other institutions where mothers' milk is expressed in advance, stored and later fed to the baby.

BACKGROUND OF THE INVENTION

Newborn infants must sometimes be cared for at a hospital for some time after birth, particularly in the case of premature or otherwise challenged babies. It is well recognized that it is advantageous for the infant to be fed its mother's natural breast milk; hence, mothers of infants requiring hospital care are encouraged to express milk for storage at the hospital, for administration to the baby when the mother is absent.

Many diseases, such as HIV, hepatitis and syphilis can be transmitted by human breast milk. For this reason, it is preferable that the baby receives only milk from its own mother. In addition, human breast milk that is improperly stored may harbour dangerous bacteria, which could harm the child.

The process for managing mothers' milk in hospital nurseries is generally as follows. Mothers are provided with a breast pump to help them express milk into appropriate containers at home. The mother is expected to label the containers with identification information and the date and time of expression then return the milk to the hospital. At the hospital, the milk is stored in a common refrigerator along with milk from other mothers.

A caregiver responsible for managing the baby's diet creates a feeding order that includes the volume of milk to be fed, and specifies any dietary supplements that must be added. It is usual practice to include an order for baby formula with the order, in case there is insufficient mother's milk available. Based on the order, units of milk are prepared for the baby and are labelled with the baby's identification, using the oldest mother's milk available.

When the baby requires feeding, the caregiver selects a prepared milk unit from the refrigerator and checks to make sure it is for the intended baby.

The selected milk unit is then fed to the baby, following a procedure that may include aspirating the baby's stomach to see if it has completely digested the previous feeding, feeding the baby the new milk, and recording the time taken and quantity fed. This information is useful for managing the overall nutrition of the infant.

There are several areas of risk with this process. It is possible that milk from the wrong mother may be selected by the caregiver; that an older milk unit might be missed, resulting in wastage; that milk may have been stored too long and may no longer be safe; and that the correct feeding procedure may not be followed. Other than training of caregivers, little is available to reduce the risk of the process.

SUMMARY OF THE INVENTION

The current invention reduces the risk of a baby receiving the wrong milk by providing apparatus and method for labelling the milk unit with a label including the baby's identification in an electronically readable form, and providing the baby with identification in electronically readable form so that the milk unit and baby's identification can be matched at the time of feeding.

In another aspect, the current invention provides a means for monitoring the storage of the mother's milk to ensure that it is correctly stored, that the storage duration is within pre-set limits, that the oldest milk for the intended baby is used first, and that the volume of mother's milk in storage at any time can be determined.

In another embodiment, the invention includes apparatus and method for ensuring that the caregiver follows the correct procedures and records the required information when the baby is fed.

The current invention also includes means for obtaining a feeding order, enduring that it is for the correct baby, that the feed volume is recoded, an that all required additives are properly noted. Advantageously, the invention provides means for ensuring that the baby's identification as noted on the feeding order is correctly matched with the mother's milk used to fill the order, and that the prepared milk is correctly labelled with the baby's identification, and further, that the amount of milk available is known at the time the order is placed, so that a contingency order for formula can be prepared if there is not sufficient milk in storage.

The invention also provides means for recording feeding orders, storage and retrieval of milk from one or more storage locations, and feeding of babies in a database, which can in turn be used to create a complete record of the feeding history for each baby.

The foregoing are accomplished with apparatus and methods described herein that herein employ electronically readable indicia to confirm the identity of the baby, the milk units, and caregivers when the mother's milk is fed to a baby. The present invention further relates to the collection, storage, and communication of information relevant to handling of the mother's milk such that complete audit trails are recorded and guidance to the caregiver is provided in order to ensure that all required procedures are executed properly.

BRIEF DESCRIPTION OF THE DRAWINGS

These and other objects, features and advantages of the present invention will become apparent upon reference to the following detailed description of the exemplary embodiment presented herein and to the drawings wherein.

DETAILED DESCRIPTION OF THE INVENTION

Figure 1:
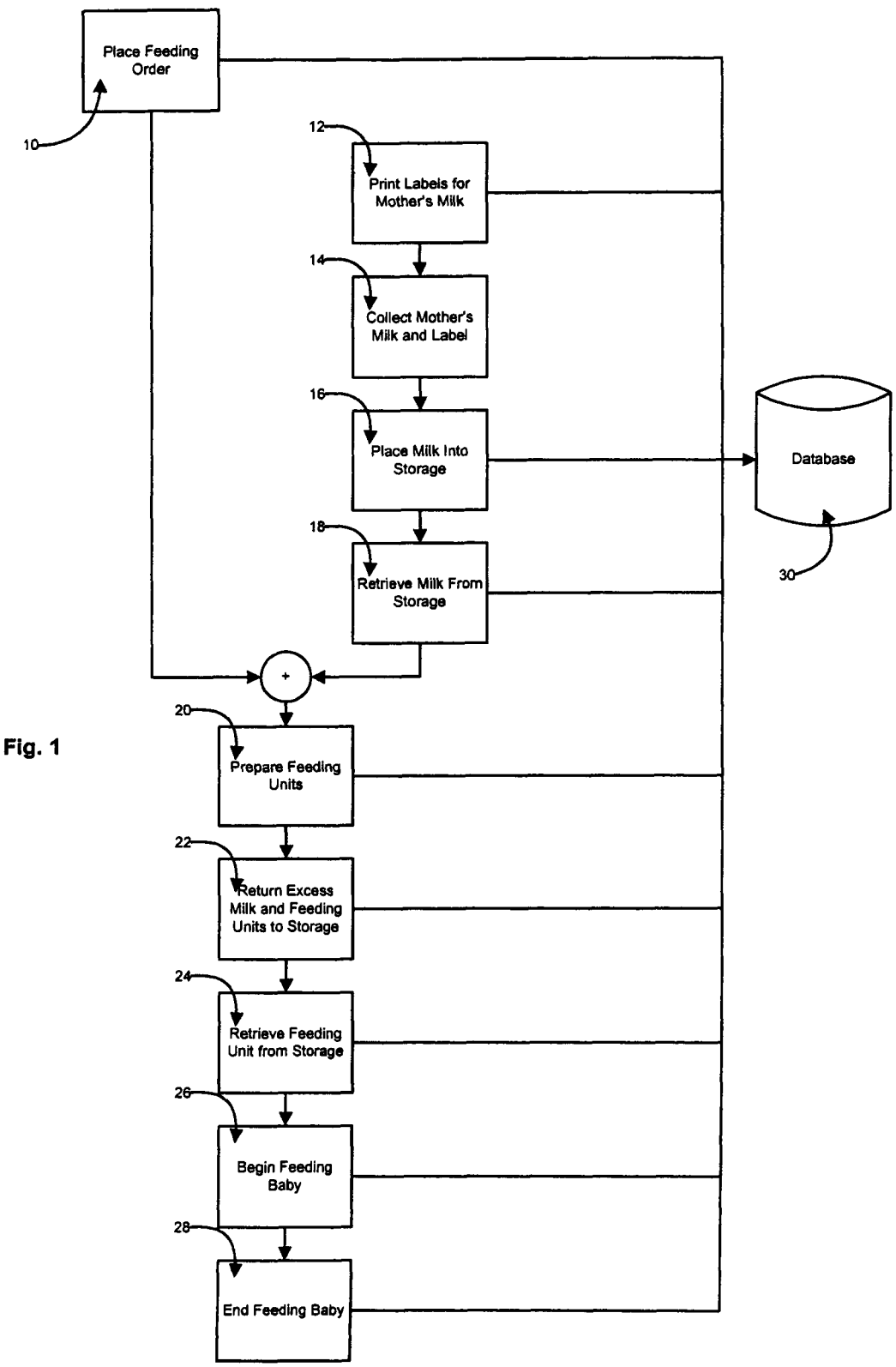
FIG. 1 illustrates a flowchart for feeding mother's milk to a baby in a hospital setting.

FIG. 1 gives an overview of one possible process for ordering, obtaining and feeding milk to a baby in a hospital setting.

Each of the steps illustrated in FIG. 1 and described in this overview are described more fully below.

The process begins with the preparation of feeding order (process 10). This feeding order includes the baby's identification, the amount of milk to be fed, and information about any dietary supplements the baby may require. Information about the feeding order is stored in database 30.

In anticipation of the baby's need for milk, the baby's mother expresses milk in advance. To ensure that the milk is correctly identified as being for a particular baby, labels for the milk bottles are printed in advance (process 12). Information about the labels printed is stored in database 30. When the baby's mother expresses and collects the milk, it is labelled with the pre-printed labels (process 14). The milk is then placed into a storage refrigerator until required (process 16). Information about the storage of the milk is recorded in database 30.

When the feeding order (process 10) is to be filled, the labelled milk is removed from the storage refrigerator (process 18). Information about the removal of the milk from storage is recorded in database 30. The milk is then prepared in accordance with the feeding order (process 20). Completion of the milk preparation is recorded in database 30. If there is excess milk, it is returned to the refrigerator, along with the prepared feedings (process 22). Information about the storage of the original milk and the prepared feedings is stored in database 30.

When the baby is to be fed, a feeding unit is retrieved from storage (process 24). Removal of the feeding unit is recorded in database 30. The feeding is started as described below (process 26). Information collected during the feeding start is recorded in database 30. Once the feeding is completed, the end of the feeding is recorded (process 28). The information collected during the end of feeding is recorded in database 30.

Figure 2:
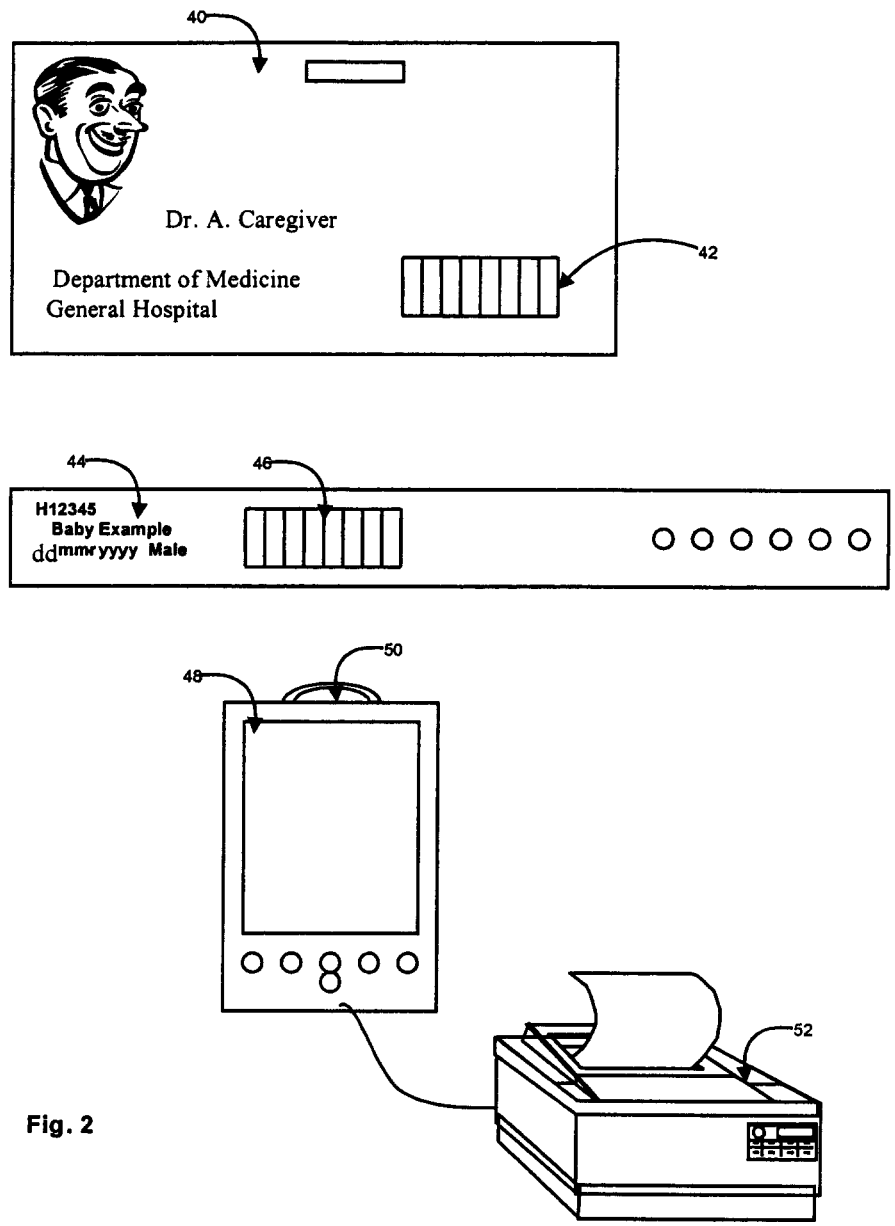
FIG. 2 is a schematic diagram of one possible apparatus for managing the feeding order preparation, label printing, feeding start and feeding completion processes of FIG. 1.

FIG. 2 illustrates apparatus suitable for implementing the ordering (process 10), label printing (process 12), begin feeding (process 26) and end feeding (process 28) parts of the method according to the invention. The apparatus includes several components that are used in conjunction to execute the steps.

Each caregiver involved in the transfusion process has an identity means 40, which includes electronically readable caregiver code 42. Caregiver code 42 may be a linear or two-dimensional barcode using any one of many common barcode formats, such as code39, code128, Interleave 2 of 5, PDF 417, Matrix code, QR code, or others. Caregiver code 42 may also be any other type of electronically readable code means such as a Radio Frequency Identification (RFID) tag. Caregiver identity means 40 may be an employee identification card or similar item, in which caregiver code 42 is embedded, or to which caregiver code 42 is applied. In the exemplary embodiment presented herein, caregiver code 42 is a barcode label encoded with a unique number or letter combination, which is applied to the caregivers' employee identification card.

Each baby to be fed wears an identification wristband 44, which includes electronically readable patient code 46. Patient code 46 may be a linear or two-dimensional barcode using any one of many common barcode formats, such as code39, code128, Interleave 2 of 5, PDF 417, Matrix code, QR code, or others. Patient code 46 may also be any other type of electronically readable code means such as a Radio Frequency Identification (RFID) tag. In the exemplary embodiment presented herein, patient code 46 is a PDF-417 barcode, in which the patient's identity number, surname, forename, date of birth and sex are encoded.

In some cases, a baby may be too small or too compromised to permit the attachment of a wristband. In such cases, patient code 46 may be printed on a label, which is applied to the baby's incubator, bassinet, or in another convenient location near the baby.

In the exemplary embodiment presented herein wristband 44 is either a PDC Smart CompuBand or PDC Smart ScanBand (Precision Dynamics Corporation, www.pdcorp.com). These wristbands incorporate RFID chips and can be programmed and printed with any standard barcodes using printers like the Zebra Technologies R402 printer/programmer (Zebra Technologies, www.zebra.com). Although one possible embodiment of the invention uses RFID wristbands, an alternative embodiment uses wristbands having printed barcodes and no RFID chips. Wristbands that may be printed with barcodes are available from many sources, including the Z-Band from Zebra technologies. The Z-Band and similar products can be printed using commonly available thermal and thermal transfer label printers.

The apparatus according to the invention also includes a portable computer, preferably a Personal Digital Assistant (PDA) 48. PDA 48 includes reader 50, which is able to read caregiver code 42 and patient code 46. Reader 50 may be a barcode scanner, a barcode imager or an RFID reader. PDA 48 is also preferably equipped with a wireless network means, a touch screen, communication means for communicating with a portable printer, and is suitable for cleaning and disinfection. In the exemplary embodiment presented herein, PDA 48 is a Symbol PPT2748, a Symbol SPT1746, a Symbol MC50, a Symbol MC3000 (Symbol Technologies Ltd, www.symbol.com), an HHP Dolphin, or an Intermec Model 700.

Included on PDA 48 is software to implement the ordering (step 10), label printing (process 12), begin feeding (process 26) and end feeding (process 28) methods in accordance with the invention, as hereinafter described.

The apparatus further includes portable printer means 52 which can communicate with PDA 48 such that PDA 48 can cause printer 52 to print labels as required. In the exemplary embodiment presented herein, printer 52 is a Zebra QL-220 (Zebra Technologies, www.zebra.com) battery powered printer, which may be connected to PDA 48 with a cable or through a wireless connection, such as a Bluetooth connection or an 802.11x connection.

Figure 3:
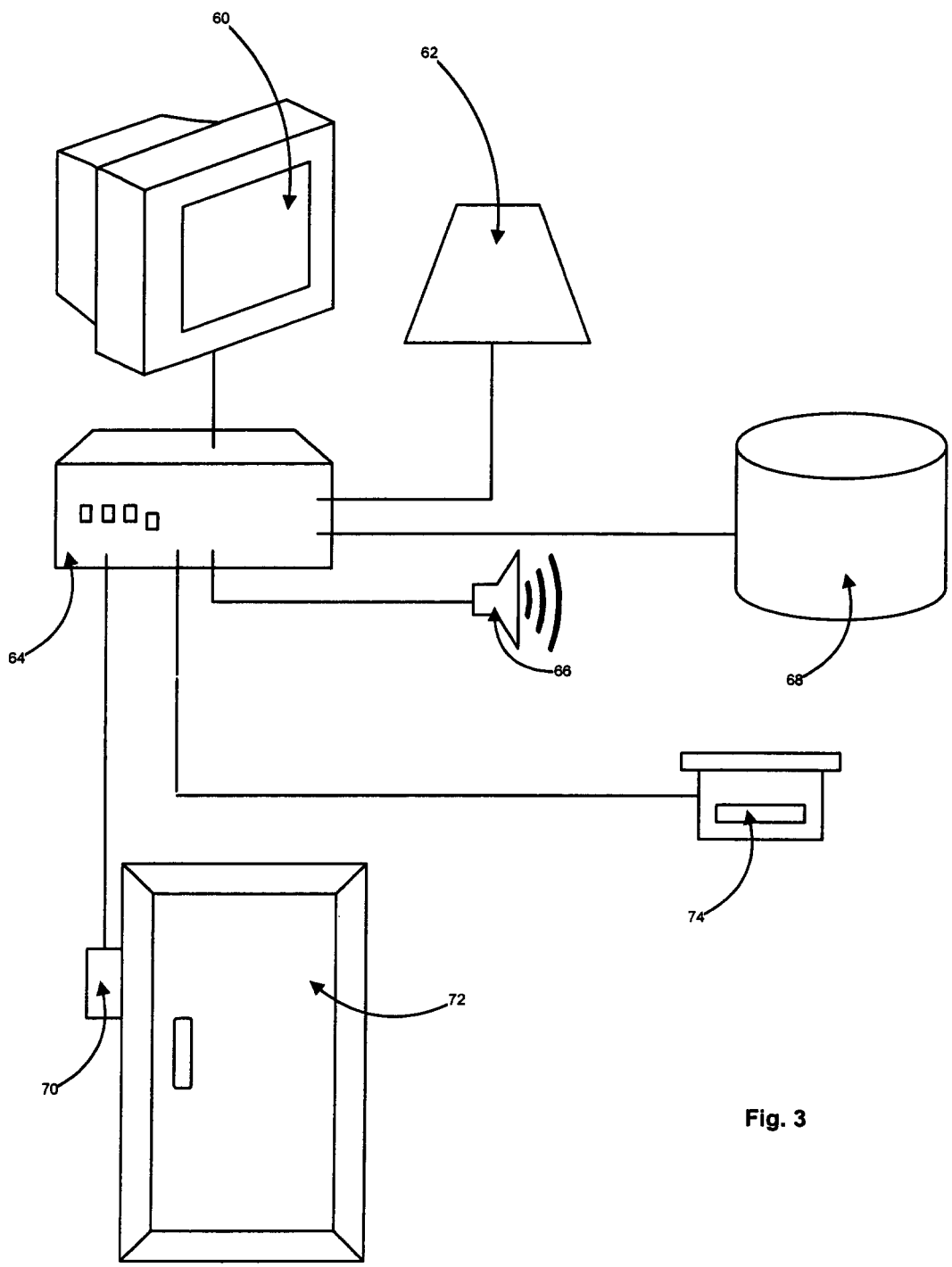
FIG. 3 is a schematic diagram of one possible apparatus for managing the milk storage and retrieval processes of FIG. 1.

FIG. 3 illustrates apparatus suitable for implementing the steps of placing milk into storage (process 16), removing milk from storage (process 18) or returning milk to storage (process 22).

Expressed mother's milk and prepared milk feeding units are stored in refrigerator 72, which is usually in a location accessible to those charged with collecting milk for feeding or for preparation. Refrigerator 72 is equipped with electronic lock 70, which in turn is connected to computer 64, such that software installed on computer 64 can lock and unlock refrigerator 72.

Also connected to computer 64 is reader 62, which may be a barcode scanner (such as the Imageteam IT 4410 High Density Image Reader, Hand Held Products, Skaneateles Falls N.Y., www.handheld.com) or RFID reader (such as the Gemini HF200, Blackroc Technology Limited, www.blackroc.com). Computer 64 is also connected to speaker 66, and disk drive 68. Database 30 is stored on disk drive 68.

Computer 64 is further connected to touch screen 60 that provides a visual display and a touch operated user interface for operating the software running on computer 64, and to weighing device 74, which can send weight information to computer 64.

In some hospitals, there may be more than one location where milk or milk feeding units are stored before fed to a baby. Milk may be moved from place to place before it is finally fed to a baby. Each time the milk is moved into or out of a refrigerator, it is important to make sure that the milk has not been out of refrigeration longer than an acceptable time, and that the milk has not passed its expiry date. For this reason, the apparatus illustrated in FIG. 3 is normally installed at every location where milk is stored, even temporarily. Each such installation will be connected to database 30 so that data may be shared among all instances of the apparatus.

Figure 4:
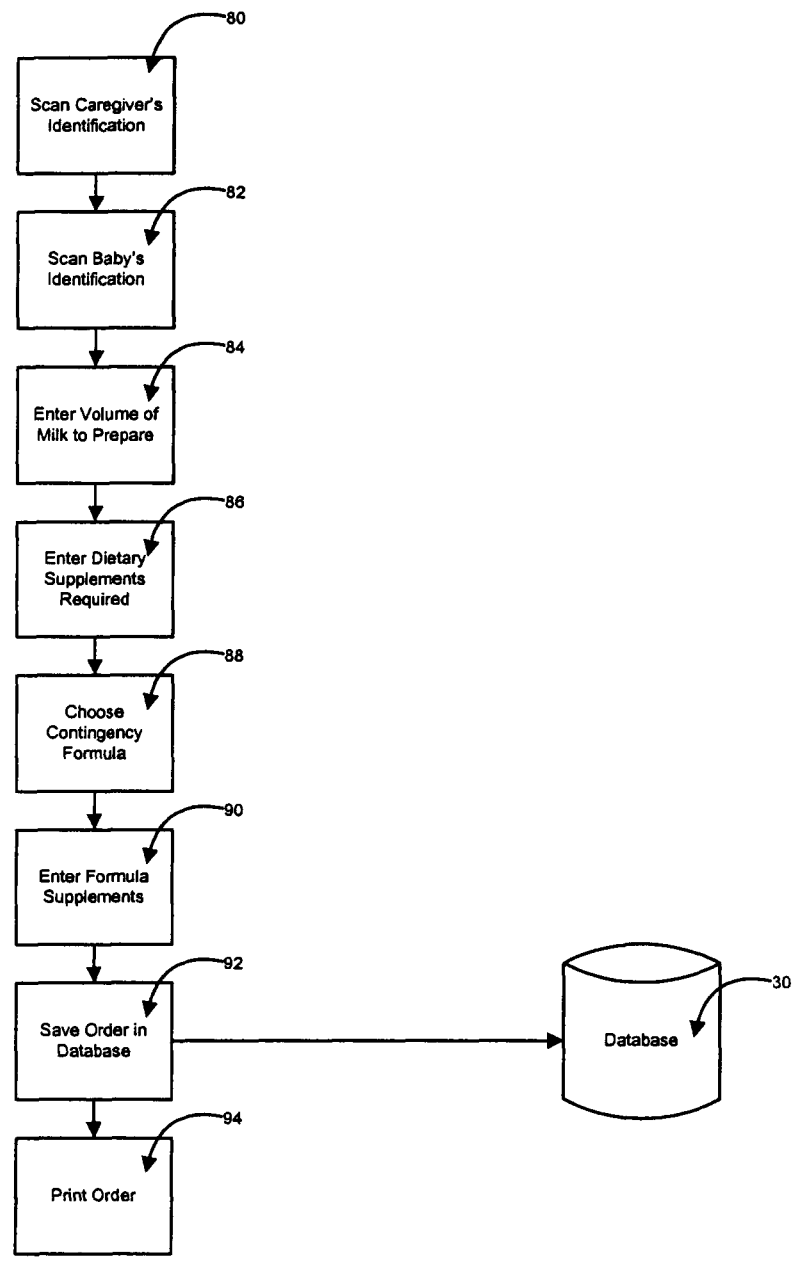
FIG. 4 illustrates a flow chart for the place feeding order process of FIG. 1.

Referring to FIG. 4, software included on PDA 48 provides means for creating a feed order (process 10). At each step in process 10, the software causes PDA 48 to display messages to the caregiver indicating the next step that the caregiver should perform. This forces the caregiver to follow a predefined procedure that is the same each time an order is created. This has the effect of allowing even inexperienced caregivers to prepare a complex order as if they have been highly trained.

In the first step of order creation process 10, PDA 48 displays a message asking the caregiver to read their caregiver code 42 (step 80). To do this, the caregiver uses reader 50 of PDA 48 and either scans caregiver code 42 (if caregiver code 42 is a barcode) or brings reader 50 within range of caregiver code 42 (if caregiver code 42 is an RFID tag).

When a caregiver code is successfully read, PDA 48 displays a message requesting the caregiver to read the baby's patient code 46 (step 82). Using reader 50 of PDA 48, the caregiver either scans patient code 46 (if patient code 46 is a barcode) or brings reader 50 within range of patient code 46 (if patient code 46 is an RFID tag). PDA 48 displays the patient identification information encoded in patient code 46. In the exemplary embodiment presented herein, this display includes the baby's identification number, surname, forename, date of birth and sex. PDA 48 displays a message asking the caregiver to confirm that the patient information is correct.

If the caregiver is satisfied that the information read from wristband 44 is correct, they press a button on the touch screen of PDA 48 to confirm that they have checked the information.

PDA 48 now displays a message asking the caregiver to enter the volume of milk to be ordered. In the exemplary embodiment, a keypad is displayed on the touch screen of PDA 48 to facilitate entry of the volume information (step 84). Once the volume information is entered correctly, the caregiver presses a button on the touch screen of PDA 48 to confirm the order volume.

PDA 48 now displays a selection of dietary supplements that the caregiver may choose to order for addition to the mother's milk (step 86). Once the required supplements have been selected (or if no supplements are required), the caregiver presses a button on the touch screen of PDA 48 to confirm the supplement requirements.

When feeding orders are placed, PDA 48 may query database 30 to determine the amount of milk available for the baby. In the exemplary embodiment, this is done by sending the data over a wireless network from PDA 48 to a computer on which is stored database 30. The volume of milk available is recorded into database 30 when milk is placed into storage as hereinafter described. If there is not sufficient milk available in storage, a message displayed on PDA 48 will ask the caregiver to prepare a contingency formula order, so that any shortage of the natural mother's milk can be made up with formula. PDA 48 displays a selection of different formulas from which the caregiver selects the most appropriate to be used for contingency (step 88). The caregiver then presses a button on the touch screen of PDA 48 to confirm the contingency formula type.

Like natural mother's milk, the formula may need to be fortified with dietary supplements. PDA 48 now displays a selection of dietary supplements that the caregiver may choose to order for addition to the formula (step 90). Once the required supplements have been selected (or if no supplements are required), the caregiver presses a button on the touch screen of PDA 48 to confirm the supplement requirements.

At this point, the software on PDA 48 saves the order information in database 30 (step 92). In the exemplary embodiment, this is done by sending the data over a wireless network from PDA 48 to a computer on which is stored database 30.

PDA 48 now displays a message prompting the caregiver to print out the order. The caregiver connects and turns on printer 52, then presses a button on the touch screen of PDA 48 to print out the order. The printed order includes the baby's identification information, the volume of milk ordered, a list of any supplements requested for the mother's milk, the type of formula to use if required, and any supplements required for the formula. In addition to this information, a two-dimensional barcode is printed on the order. This two-dimensional barcode (which may be a PDF-417, OR, Matrix Code, Aztec, or other two-dimensional barcode) encodes at least the baby's identification, and may also encode the volume, supplements, formula, and formula supplements information. The two-dimensional barcode permits electronic reading and confirmation of the order information when the milk is prepared (process 20).

Figure 5:
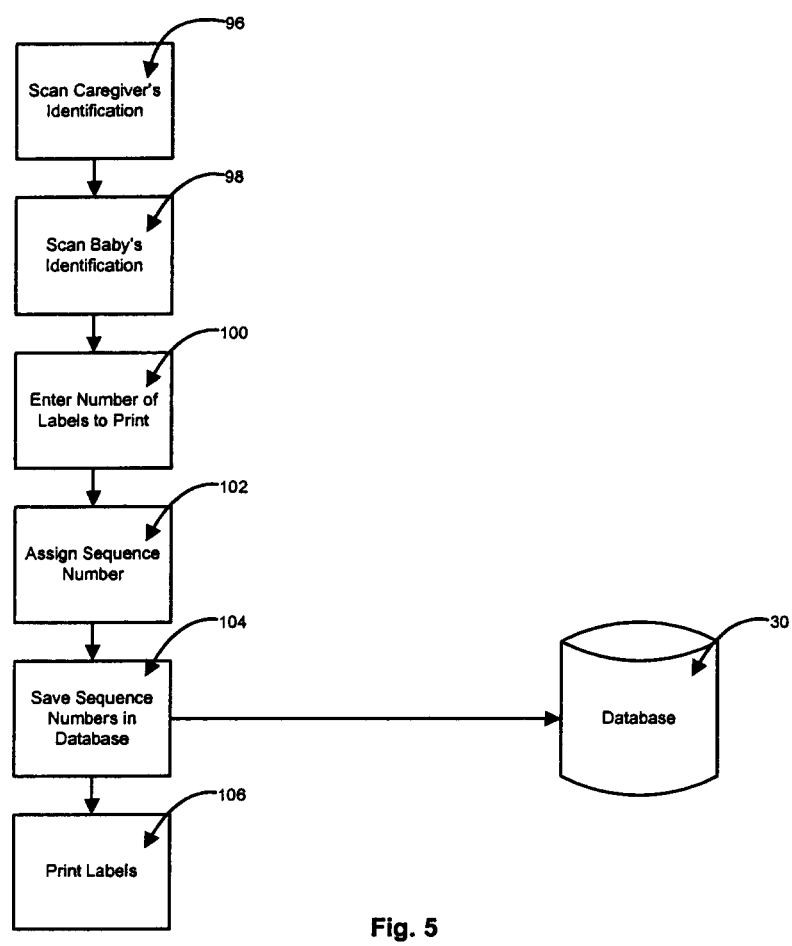
FIG. 5 illustrates a flow chart for the print labels process of FIG. 1.

Referring to FIG. 5, software included on PDA 48 provides means for printing labels for the bottles in which the baby's mother will collect milk she expresses (process 12).

PDA 48 displays a message asking the caregiver to read their caregiver code 42 (step 96). To do this, the caregiver uses reader 50 of PDA 48 and either scans caregiver code 42 (if caregiver code 42 is a barcode) or brings reader 50 within range of caregiver code 42 (if caregiver code 42 is an RFID tag).

When a caregiver code is successfully read, PDA 48 displays a message requesting the caregiver to read the baby's patient code 46 (step 98). Using reader 50 of PDA 48, the caregiver either scans patient code 46 (if patient code 46 is a barcode) or brings reader 50 within range of patient code 46 (if patient code 46 is an RFID tag). PDA 48 displays the patient identification information encoded in patient code 46. In the exemplary embodiment presented herein, this display includes the baby's identification number, surname, forename, date of birth and sex. PDA 48 displays a message asking the caregiver to confirm that the patient information is correct.

If the caregiver is satisfied that the information read from wristband 44 is correct, they press a button on the touch screen of PDA 48 to confirm that they have checked the information.

PDA 48 next displays a message asking the caregiver to select the number of labels to be printed (step 100). The software on PDA 48 then assigns a sequence number for each of the labels to be printed (step 102), and sends this information to database 30 (step 104). In the exemplary embodiment, this is done by sending the data over a wireless network from PDA 48 to a computer on which is stored database 30.

The caregiver connects and turns on printer 52, then presses a button on the touch screen of PDA 48 to print out the labels (step 106). Each printed label includes the baby's identification and the assigned sequence number, and also includes a two-dimensional barcode that encodes the baby's identification and the sequence number.

Figure 6:
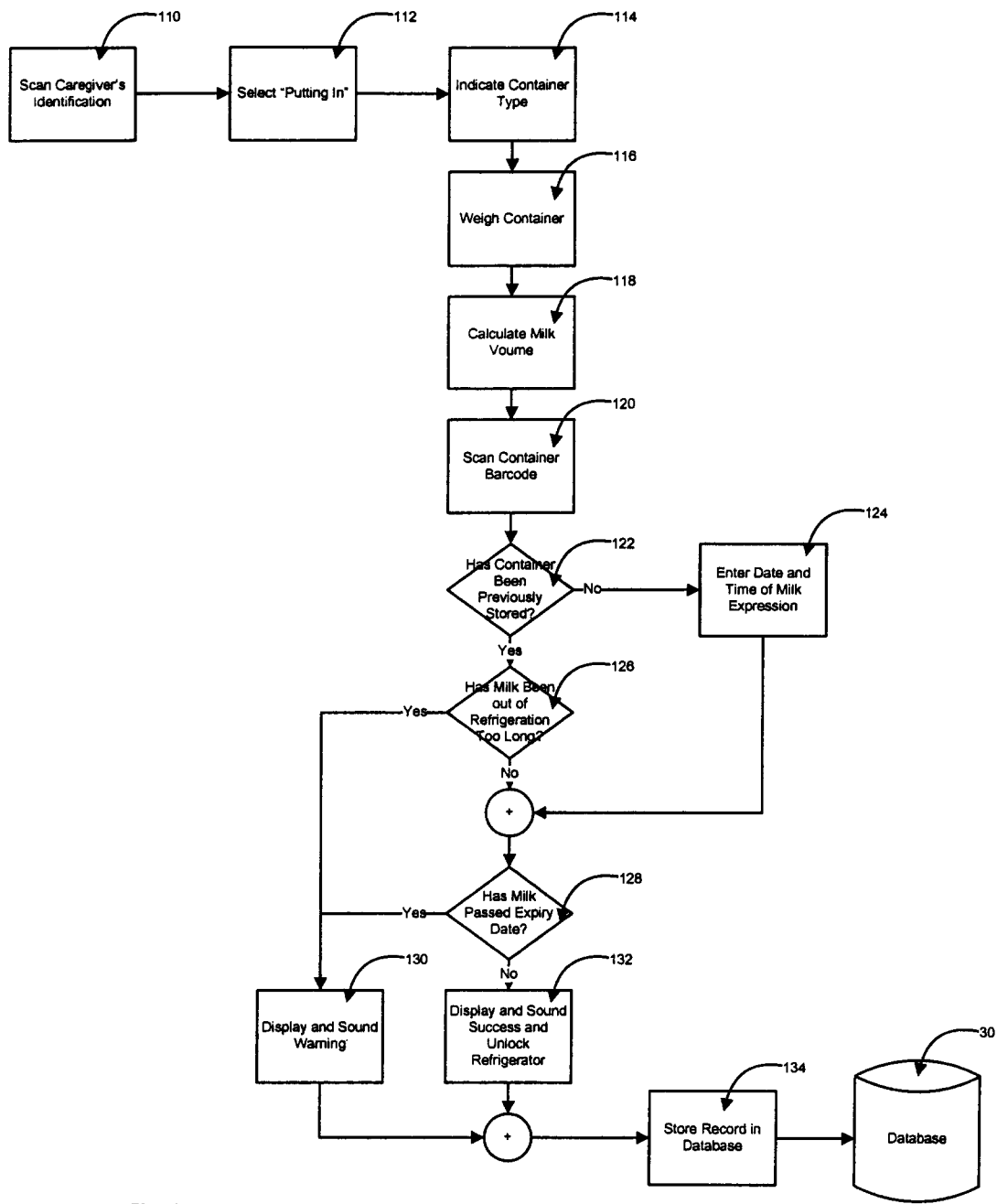
FIG. 6 illustrates a flow chart for the place milk into storage or return milk to storage processes of FIG. 1.

Referring to FIG. 6, software on computer 64 provides means for controlling the storage of mothers' milk in refrigerator 72, either when it is first received (process 16) or when it is returned (process 22) as hereinafter described.

Computer 64 displays a message on touch screen display 60 asking the caregiver to scan their caregiver code 42. To do this, the caregiver uses reader 62 and either scans caregiver code 42 (if caregiver code 42 is a barcode) or brings caregiver code 42 within range of reader 62 (if caregiver code 42 is an RFID tag) (step 110).

When a caregiver code is successfully read, computer 64 displays two buttons on touch screen display 60, and displays a prompt asking the caregiver to indicate if they are putting milk into the refrigerator or taking milk out of the refrigerator. For this process (process 16 or process 22), milk is being put into the refrigerator, so the caregiver selects the 'putting in' option (step 112).

Computer 64 now displays a selection of different container types on touch screen display 60. The caregiver touches the container type to tell computer 64 what type of container is to be stored (step 114).

Computer 64 now displays a prompt on touch screen display 60 asking the caregiver to place the milk container on electronic scale 74 (step 116). Scale 74 measures the weight of the container, and then subtracts from this weight the pre-determined weight of the empty container, to calculate the weight of milk in the container. This weight is multiplied by a factor equal to the density of milk to arrive at a volume of milk (step 118).

Computer 64 now causes touch screen display 60 to display a prompt asking the caregiver to scan the two-dimensional barcode printed on the container label (step 120). This label is either one of the labels printed as described in process 12 above, or a milk unit label printed during process 20.

Once the container barcode is read, computer 64 searches database 30 to see if the milk unit has ever been stored in the refrigerator, by looking for a record of a milk unit having the same assigned sequence number as that contained in the label (step 122). If no previous record is found, it is assumed that this is a new unit of milk, in which case computer 64 displays a prompt on touch screen display 60 asking the caregiver to enter the date and time that the milk was expressed (step 124). If a previous record for the milk unit is found, the last date and time that the milk was removed from refrigerator 72 is retrieved. This date and time is compared to the current date and time to determine how long the milk has been outside of refrigeration (step 126). If the milk has been outside of refrigeration too long, a warning is sounded through speaker 66 and a warning message is displayed on touch screen display 60 (step 130). If the milk has not been out of refrigeration too long, or if the milk is being stored for the first time, the date and time of the expression of the milk is compared to the current date and time to see if the milk has passed its expiry date (step 128). If the milk has passed its expiry date, a warning is sounded through speaker 66 and a warning message is displayed on touch screen display 60 (step 130). If the milk has not yet passed its expiry date, a message is displayed on touch screen display 60 instructing the caregiver to put the milk into the refrigerator and door lock 70 is released so that the caregiver can open refrigerator 72 and place the milk into storage (step 132). When either the warning message in step 130 or the success message in step 132 is displayed, a record is stored in database 30, including the time and date, the caregiver's identification, container type, container weight, milk volume, time and date of expression (if entered), and all information in the container barcode (which includes the baby's identification and the sequence number) (step 134).

Figure 7:
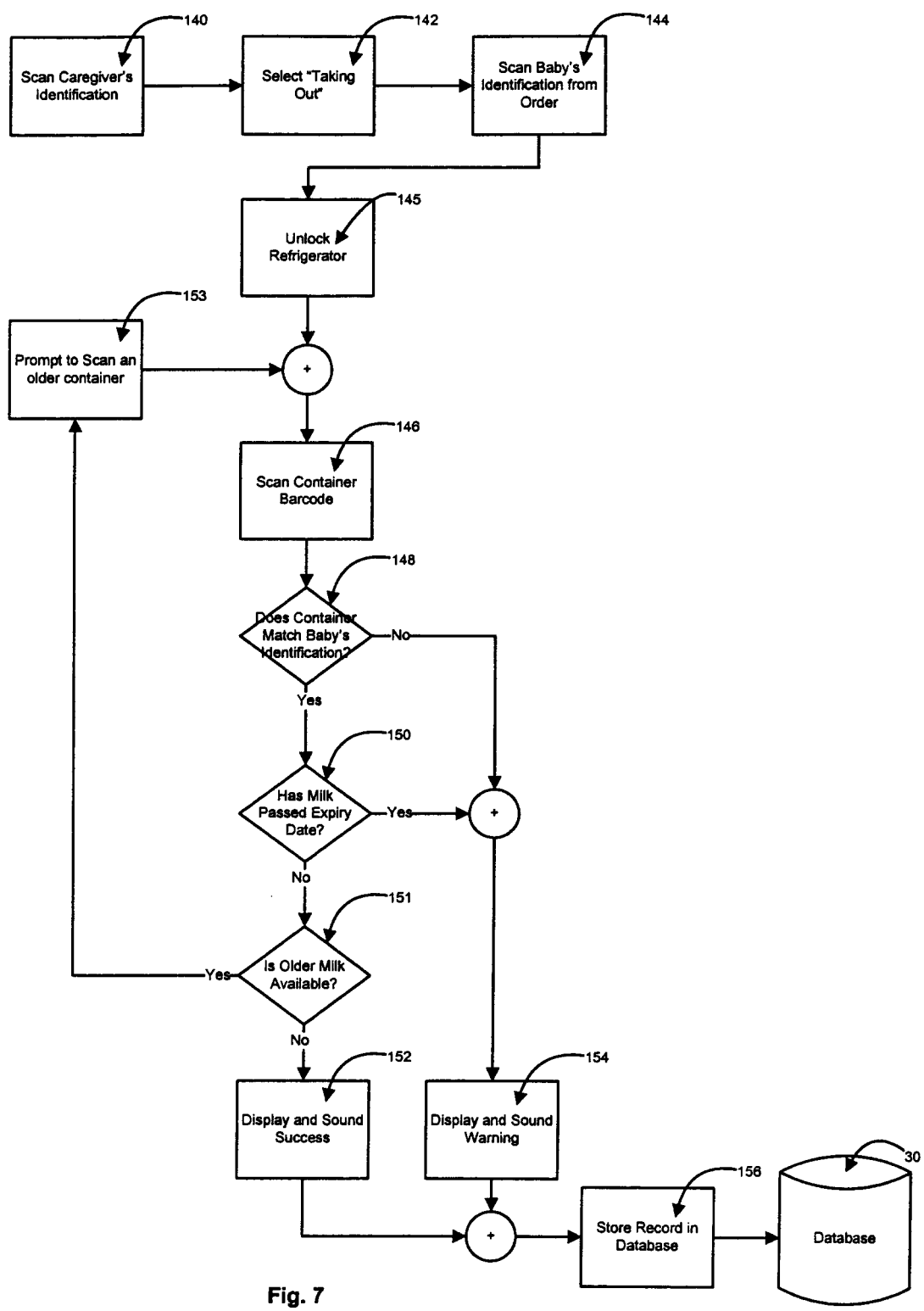
FIG. 7 illustrates a flow chart for the retrieve milk or feeding units from storage processes of FIG. 1.

Referring to FIG. 7, software on computer 64 provides means for controlling the retrieval of milk from refrigerator 72.

Computer 64 displays a message on touch screen display 60 asking the caregiver to scan their caregiver code 42. To do this, the caregiver uses reader 62 and either scans caregiver code 42 (if caregiver code 42 is a barcode) or brings caregiver code 42 within range of reader 62 (if caregiver code 42 is an RFID tag) (step 110).

When a caregiver code is successfully read, computer 64 displays two buttons on touch screen display 60, and displays a prompt asking the caregiver to indicate if they are putting milk into the refrigerator or taking milk out of the refrigerator. For this process (process 18 or process 24), milk is being taken out of refrigerator 72, so the caregiver selects the 'taking out' option (step 142).

Computer 64 now displays a message asking the caregiver to scan the baby's identification (step 144). This may be the two-dimensional barcode on a milk order barcode that is produced when the feeding order is created as described in process 10, above, or may be a copy of the baby's wristband barcode. Once a baby's identification barcode is read, refrigerator lock 70 is de-activated, permitting the caregiver to retrieve milk units from refrigerator 72 (step 145).

Computer 64 displays a message on touch screen display 60 asking the caregiver to scan the barcode on a milk unit to be removed from refrigerator 70. When a milk unit barcode is scanned (step 146), computer 64 compares the baby's identification encoded in the barcode on the milk unit to the baby's identification read from the barcode in step 144 (step 148). If the identification from the two barcodes does not match, a warning is sounded with speaker 66 and a warning message is displayed on touch screen display 60 (step 154). If the identification confirms that the milk unit is intended for the baby identified in step 144, the date and time of the expression of the milk is compared to the current date and time to see if the milk has passed its expiry date (step 150). If the milk has passed its expiry date, a warning is sounded through speaker 66 and a warning message is displayed on touch screen display 60 (step 154). Computer 64 now checks database 30 to see if the milk unit is the oldest milk unit available in the refrigerator, as determined by the data and time of expression entered when the milk is first stored in the refrigerator (step 151). If the milk is not the oldest available, a prompt is displayed on touch screen display 60 asking the user to scan a different milk unit (step 153). If the milk unit scanned is the oldest available, and if the milk has not yet passed its expiry date, a message is displayed on touch screen display 60 informing the caregiver that the correct milk was selected and is suitable for use (step 152). When either the warning message in step 154 or the success message in step 152 is displayed, a record is stored in database 30, including the time and date, the caregiver's identification, and the baby's identification (step 156).

Figure 8:
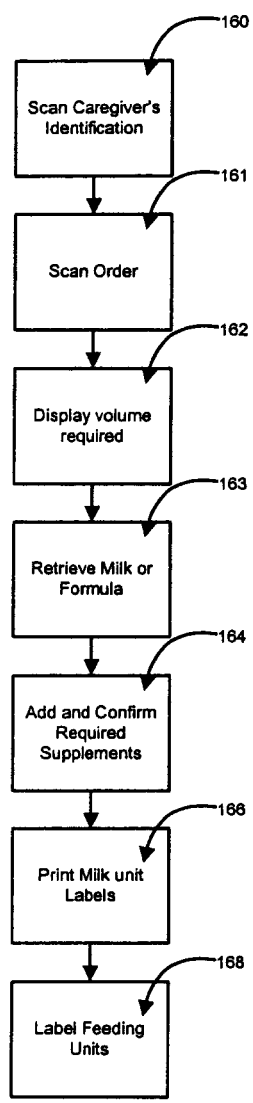
FIG. 8 illustrates a flow chart for the preparation of feeding units process of FIG. 1.

FIG. 8 describes the steps followed when preparing a feeding unit (process 20). Software to manage this process can be installed on any typical desktop computer equipped with a label printer such as a Zebra TLP-2824 thermal label printer (Zebra Technologies, www.zebra.com) and a barcode scanner capable of reading two-dimensional barcodes, such as the Imageteam IT 4410 High Density Image Reader, (Hand Held Products, Skaneateles Falls N.Y., www.handheld.com).

The preparation software first displays a message asking the caregiver to scan their caregiver code 42 (step 160), then scan the two-dimensional barcode on the order produced in process 10 as described above (step 161). The computer will then display the details of the order, including the amount of milk required (step 162). The caregiver will then retrieve the required amount of milk from refrigerator 72 (process 18). If there is not enough useable mother's milk available, the caregiver will obtain the contingency formula that was specified in the order (step 163).

Next the caregiver prepares the milk and/or formula by adding the dietary supplements specified in the order. Each of the supplements added are confirmed with the preparation software (step 164).

When the milk had been prepared and decanted into containers for each feeding unit, the preparation software is used to print the required number of feeding unit labels (step 166). The labels are then applied to the feeding units (step 168).

Figure 9:
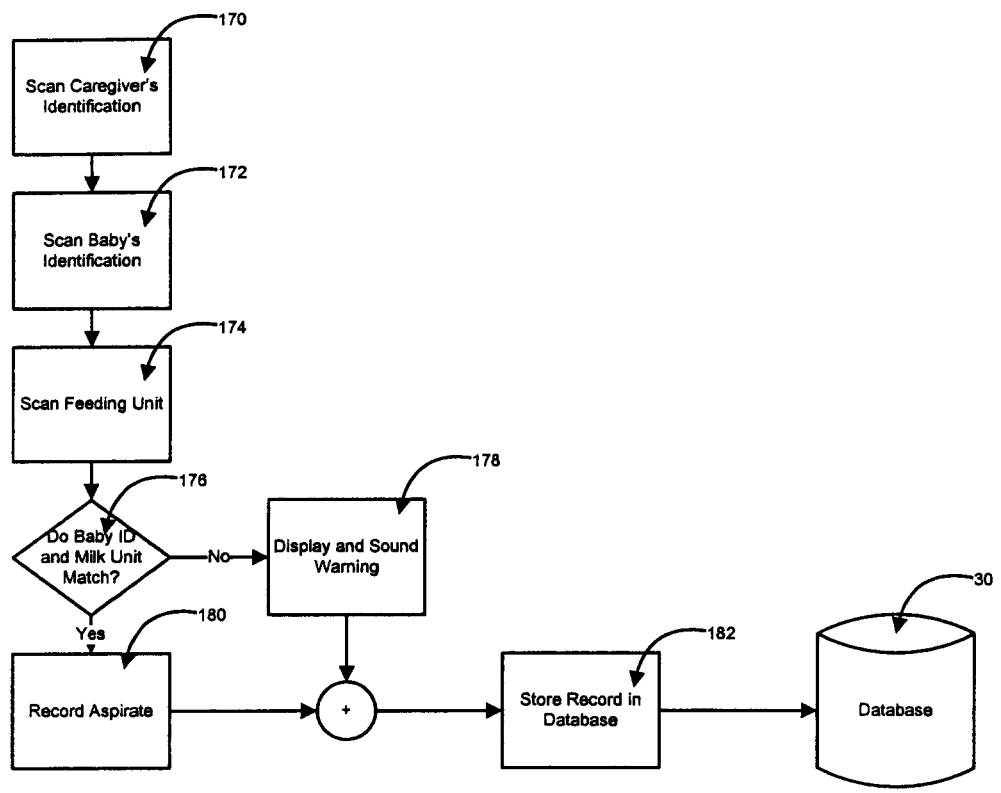
FIG. 9 illustrates a flow chart for the begin feeding baby process of FIG. 1.

Referring to FIG. 9, software included on PDA 48 provides means for verifying the baby's identity and beginning the process of feeding a baby with the prepared feeding unit (process 26).

PDA 48 displays a message asking the caregiver to read their caregiver code 42 (step 170). To do this, the caregiver uses reader 50 of PDA 48 and either scans caregiver code 42 (if caregiver code 42 is a barcode) or brings reader 50 within range of caregiver code 42 (if caregiver code 42 is an RFID tag).

When a caregiver code is successfully read, PDA 48 displays a message requesting the caregiver to read the baby's patient code 46 (step 172). Using reader 50 of PDA 48, the caregiver either scans patient code 46 (if patient code 46 is a barcode) or brings reader 50 within range of patient code 46 (if patient code 46 is an RFID tag). PDA 48 displays the patient identification information encoded in patient code 46. In the exemplary embodiment presented herein, this display includes the baby's identification number, surname, forename, date of birth and sex. PDA 48 displays a message asking the caregiver to confirm that the patient information is correct.

If the caregiver is satisfied that the information read from wristband 44 is correct, they press a button on the touch screen of PDA 48 to confirm that they have checked the information.

PDA 48 next displays a message asking the caregiver to scan the two-dimensional barcode on the feeding unit (step 174). The software on PDA 48 compares the baby's identification as read from patient code 46 with the baby's identification as read from the barcode on the feeding unit (step 176). If the identification does not match, PDA 48 sounds a warning and displays an error message (step 178). If the identification does match, PDA 48 displays a prompt asking if the baby's stomach is aspirated (to remove undigested milk), and if so, to enter the volume of the aspirate and indicate if the undigested milk was returned to the baby's stomach (step 180). Entry is facilitated with touch-screen numeric keypad displayed on the screen of PDA 48.

When either the warning message in step 178 is displayed, or when the amount of aspirate is recorded, a record is stored in database 30, including the time and date, the caregiver's identification, the baby's identification, the sequence number for the milk unit fed, and the amount of aspirate recovered and/or returned (step 182). In the exemplary embodiment, this is done by sending the data over a wireless network from PDA 48 to a computer on which is stored database 30.

Figure 10:
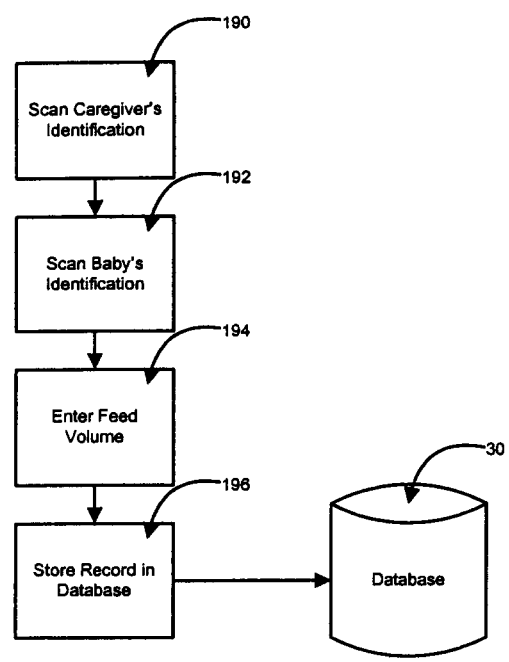
FIG. 10 illustrates a flow chart for the end feeding baby process of FIG. 1.

Referring to FIG. 10, software included on PDA 48 provides means for finishing the process of feeding a baby (process 28).

PDA 48 displays a message asking the caregiver to read their caregiver code 42 (step 190). To do this, the caregiver uses reader 50 of PDA 48 and either scans caregiver code 42 (if caregiver code 42 is a barcode) or brings reader 50 within range of caregiver code 42 (if caregiver code 42 is an RFID tag).

When a caregiver code is successfully read, PDA 48 displays a message requesting the caregiver to read the baby's patient code 46 (step 192). Using reader 50 of PDA 48, the caregiver either scans patient code 46 (if patient code 46 is a barcode) or brings reader 50 within range of patient code 46 (if patient code 46 is an RFID tag). PDA 48 displays the patient identification information encoded in patient code 46. In the exemplary embodiment presented herein, this display includes the baby's identification number, surname, forename, date of birth and sex. PDA 48 displays a message asking the caregiver to confirm that the patient information is correct.

If the caregiver is satisfied that the information read from wristband 44 is correct, they press a button on the touch screen of PDA 48 to confirm that they have checked the information.

PDA 48 next displays a message asking the caregiver to enter the volume of milk delivered to the baby in the course of the feeding (step 194). Entry is facilitated with touch-screen numeric keypad displayed on the screen of PDA 48.

When the feeding volume is entered, a record of the feeding completion is stored in database 30, including the time and date, the baby's identification and the volume of milk delivered to the baby. In the exemplary embodiment, this is done by sending the data over a wireless network from PDA 48 to a computer on which is stored database 30.

From the detailed description above, it can be seen that the invention provides means for recording every step in the storage, preparation and delivery of mothers' milk to babies in hospital care, including all movements of the milk prior to feeding. Each of the steps is recorded in database 30. It will be obvious to one skilled in the art that data collected in this way can easily be read into a database program such as Microsoft Access (Microsoft Corporation, www.microsoft.com) from which various reports can be created. It is also possible, with the same database program, to determine the complete history of any particular baby's feedings. Such data can easily be correlated with a baby's weight to provide valuable information for management of the baby's nutrition.

Many different adaptations and variations of the subject invention are possible without departing from the scope and spirit of the present invention, therefore, the present invention should be limited only by the scope of the appended claims. For example the delivery of blood or drugs to patients presents many of the same problems as those described herein for blood transfusion. It would be clear to one skilled in the art that a system similar to that described here could be used to control the collection and administration of drugs, or transfusion of blood to a patient.

Therefore, while the present invention has been described in terms of various preferred embodiments, it will be appreciated by one of ordinary skill that the spirit and scope of the invention is not limited to those embodiments, but extend to the various modifications and equivalents as defined in the appended claims.

What is claimed is:

1. A method for managing the acquisition and distribution of mother's milk in a hospital setting, comprising the steps of:

a) providing a recipient with an electronically readable identification means;
b) reading the recipient's identification from the identification means with a reader;
c) printing labels with the recipient's identification in an electronically readable form with a printer and storing information about the labels in a database stored on a computer;
d) collecting milk into containers and recording in a computer database the date and time at which the milk is expressed;
e) labeling the containers with the printed labels;
f) storing the containers in a refrigerator and recording in a computer database the time at which the milk is stored in the refrigerator;
g) reading the recipient's identification from the identification means with a reader when feeding of the milk begins;
h) reading the recipient's identification from the printed label with a reader when feeding of the milk begins;
i) using the computer to compare the recipient's identification read from the identification means to the recipient's identification read from the printed label to insure that the correct containers are fed to the recipient and;
j) using the computer database to compare the date and time at which the milk was expressed to the current date and time to check if the milk has passed its expiry date.

2. The method according to claim 1 including the step of initiating an alarm electronically connected to the computer in response to a mismatch between the recipient's identification read from the identification means and the recipient's identification read from the printed label during the comparing step.

3. The method according to claim 1 including the steps of:
a) generating a milk request slip for the recipient, the milk request slip comprising electronically readable indicia comprising the recipient's identification information;
b) retrieving the container of milk from the refrigerator and using the computer to verify the milk container's identity by comparing the recipient's identification information on the milk request slip with the recipient's identification information on the label applied to the container; and
c) using the computer to compare the recipient's identification information from the electronically readable indicia on the request slip with the electronically readable indicia on the label applied to the container.

4. The method according to claim 3 including the step of initiating an alarm electronically connected to the computer in response to a mismatch between the recipient's identification on the milk request slip and the recipient's identification on the label applied to the container.

5. The method according to claim 3 including the step of initiating an alarm electronically connected to the computer in response to a mismatch between the recipient's identification information from the electronically readable indicia on the request slip with the electronically readable indicia on the label applied to the container.

6. The method according to claim 1 including the step of weighing each container to determine the volume of milk in each container and recording in the computer database the volume of milk available.

7. The method according to claim 6 including the steps of:
a) obtaining an order for prepared milk to be fed to the recipient, wherein the order includes instructions for dietary supplements to be added to the milk to create prepared milk and the volume of prepared milk to be fed to the recipient; and
b) checking the database to see if there is sufficient milk to fill the order.

8. The method according to claim 7 including the step of providing an electronic notification through the computer that a formula order is required if there is not a sufficient volume of milk stored to fill the milk order.

9. The method according to claim 8 including the steps of:
a) retrieving the mother's milk from the refrigerator;
b) preparing the milk as specified in the order by adding dietary supplements to create prepared milk;
c) putting the prepared milk into secondary containers;
d) labeling the secondary containers with a label including electronically readable indicia comprising a recipient's identification information;
e) electronically reading the indicia on the recipient's identification means and electronically reading the indicia on the secondary container with a reader prior to feeding of the prepared milk to the recipient; and
f) initiating an electronic warning through the computer if the indicia read from the recipient's identification means does not match the indicia read from the secondary container.

10. A method for managing the acquisition and distribution of mother's milk, comprising the steps of:
a) identifying on a recipient electronically readable indicia comprising recipient identification information for the recipient and storing the recipient identification information in a database stored on a computer;
b) collecting milk expressed by the recipient's mother into a container and recording in the computer database the date and time at which the milk is expressed;
c) labeling the container with electronically readable indicia comprising the recipient's identification information;
d) storing the container of milk;
e) recording the time at which the milk is stored in the refrigerator in the computer database;
f) generating a milk request slip for the recipient, the milk request slip comprising electronically readable indicia comprising the recipient's identification information;
g) retrieving the container of milk and referring to the computer database to verify the milk container's identity by comparing the recipient's identification information on the milk request slip with the recipient's identification information on the label applied to the container; and
h) comparing the recipient's identification information on the recipient with the electronically readable indicia on the label applied to the container; and
i) using the computer database to compare the date and time at which the milk was expressed to the current date and time to check if the milk has passed its expiry date.

11. The method according to claim 10 including the step of initiating an alarm electronically connected to the computer in response to a mismatch between the recipient's identification information on the milk request slip and the recipient's identification information on the label applied to the container.

12. The method according to claim 10 including the step of initiating an alarm electronically connected to the computer in response to a mismatch between the recipient's identification information on the recipient and the recipient's identification information on the label applied to the container.

13. A method for managing the acquisition and distribution of mother's milk, comprising the steps of:
   a) labeling containers of mothers' milk with electronically readable indicia, wherein the indicia includes a unique identifying code;
   b) recording the unique identifying code and the date and time of milk expression in a database stored on a computer;
   c) storing the milk for later use;
   d) removing the milk from storage when required; and
   e) retrieving the date and time of expression of the milk from the database, using the computer to calculate the time elapsed since the milk was expressed, and providing an electronic warning through the computer if the elapsed time since expression is more than a pre-determined value.

14. The method according to claim 13 including the steps of:
   a) recording the date and time when milk is removed from storage in a database;
   b) returning unused milk to storage; and
   c) calculating the time elapsed since the milk was removed from storage and providing an electronic warning through the computer if the elapsed time is more than a pre-determined value.

* * * * *